US012268464B2

(12) United States Patent
Krueger (10) Patent No.: US 12,268,464 B2
(45) Date of Patent: Apr. 8, 2025

(54) SUBJECT POSE CLASSIFICATION USING JOINT LOCATION COORDINATES (71) Applicant: KONINKLIJKE PHILIPS N.V., Eindhoven (NL)

(72) Inventor: Sascha Krueger, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 259 days.

(21) Appl. No.: 17/775,696

(22) PCT Filed: Nov. 3, 2020

(86) PCT No.: PCT/EP2020/080718
§ 371 (c)(1),
(2) Date: May 10, 2022

(87) PCT Pub. No.: WO2021/094123
PCT Pub. Date: May 20, 2021

(65) Prior Publication Data
US 2022/0405922 A1   Dec. 22, 2022

(30) Foreign Application Priority Data
Nov. 12, 2019   (EP) ..................... 19208451

(51) Int. Cl.
A61B 5/00     (2006.01)
A61B 6/04     (2006.01)
(Continued)

(52) U.S. Cl.
CPC .......... *A61B 5/0033* (2013.01); *A61B 6/0407* (2013.01); *G06T 7/0012* (2013.01);
(Continued)

(58) Field of Classification Search
None
See application file for complete search history.

(56) References Cited

U.S. PATENT DOCUMENTS 10,229,489 B1    3/2019   Rush et al.
2015/0092998 A1  4/2015   Liu et al.
(Continued)

FOREIGN PATENT DOCUMENTS

EP   2954843 A1     12/2015
WO   2008139374 A1  11/2008

OTHER PUBLICATIONS

Wen Wang et al "Posture Recognition in CT Scanning Based on HOG Feature and Mixture-of parts Model" Proceedings of the 2019 International Conf. on Intelligent Medicine and Image Processing Apr. 19, 2019 p. 62-66.
(Continued)

*Primary Examiner* — Darryl V Dottin (57) ABSTRACT

Disclosed herein is a medical instrument (100, 300). Execution of the machine executable instructions causes a processor (106) to: receive (206) a set of joint location coordinates (128) for a subject (118) reposing on a subject support (120), receive (207) a body orientation (132) in response to inputting the set of joint location coordinates into a predetermined logic module (130), calculate (208) a torso aspect ratio (134) from set of joint location coordinates. If (210) the torso aspect ratio is greater than a predetermined threshold (136) then (212) the body pose of the subject is a decubitus pose. Execution of the machine executable instructions further cause the processor to assign (220) the body pose as being a supine pose if the subject is face up on the subject support or assign (222) the body pose as being a prone pose if the subject is face down on the subject support if the torso aspect ratio is less than or equal to the predetermined threshold. Execution of the machine executable instructions further cause the processor to generate (216) a subject pose label (142).

15 Claims, 6 Drawing Sheets (51) Int. Cl.
  *G06T 7/00* (2017.01)
  *G06V 10/764* (2022.01)
  *G06V 10/82* (2022.01)
  *G06V 40/10* (2022.01)
  *G06V 40/16* (2022.01)
  *G16H 30/20* (2018.01)

(52) U.S. Cl.
  CPC ............ *G06V 10/764* (2022.01); *G06V 10/82* (2022.01); *G06V 40/10* (2022.01); *G06V 40/16* (2022.01); *G16H 30/20* (2018.01); *G06T 2207/10081* (2013.01); *G06T 2207/10088* (2013.01); *G06T 2207/10104* (2013.01); *G06T 2207/10108* (2013.01); *G06T 2207/10116* (2013.01)

(56) References Cited

U.S. PATENT DOCUMENTS

| | | |
|---|---|---|
| 2016/0213329 A1 | 7/2016 | Dirkes |
| 2016/0306924 A1 | 10/2016 | Singh |
| 2016/0367169 A1 | 12/2016 | Hardie et al. |
| 2017/0205478 A1 | 7/2017 | Brinker et al. |
| 2019/0000564 A1* | 1/2019 | Navab .................. H04N 13/254 |
| 2019/0183439 A1* | 6/2019 | Joerger .................. A61B 6/545 |

OTHER PUBLICATIONS

Shuangjun Liu et al "In Bed Pose Estimation: Deep Learning with Shallow Dataset" Nov. 3, 2017 Cornell University Library.
International Search Report and Written Opinion from PCT/EP2020/080718 mailed Jan. 24, 2021.

* cited by examiner

SUBJECT POSE CLASSIFICATION USING JOINT LOCATION COORDINATES

CROSS REFERENCE TO RELATED APPLICATIONS

This application is a U.S. national phase application of International Application No. PCT/EP2020/080718 filed on Nov. 3, 2020, which claims the benefit of EP application Ser. No. 19/208,451.5 filed on Nov. 12, 2019 and is incorporated herein by reference.

FIELD OF THE INVENTION

The invention relates to medical imaging and radiotherapy, in particular to the positioning of a subject.

BACKGROUND OF THE INVENTION

In medical imaging modalities such as magnetic resonance imaging, as well as in radiotherapy, the proper placement of the subject prior to the procedure is critical. Otherwise the subject could be improperly imaged or the wrong portion of a subject could be irradiated.

United States patent application US 2015/0092998 A1 discloses a posture detection method and system. The posture detection method includes: obtaining skeleton data of a target person; analyzing the skeleton data to obtain actual posture information of the target person; and recording the actual posture information of the target person. The posture information is recorded automatically, so that a doctor does not need to record the posture information manually. Therefore, scanning missing or wrong scanning direction caused by inconformity between the real posture of the patient and the recorded posture information may be avoided, which ensures the reliability of medical diagnosis.

SUMMARY OF THE INVENTION

The invention provides for a medical instrument, a computer program product, and a method in the independent claims. Embodiments are given in the dependent claims.

The proper determination of a subject pose is important for ensuring that a correct patient coordinate system is used during either medical imaging or radiotherapy. Often times it is difficult to properly classify a pose of a subject. For example, injured or sick patients may have a difficult time assuming a particular pose. Other time the operator of a medical instrument may incorrectly note the pose of a subject. Embodiments provide a means for automatically generating a subject pose label for a subject on a subject support. A set of joint location coordinates are received. These may be coordinates which indicate location of the major joints of a subject's skeletal system. The relative position of the joint location coordinates enables the determination if the subject is feet first or head first on the subject support. A predetermined logic module may be programmed to make this determination.

The determination if the subject is feet first or head first may in some examples be relative to a chosen coordinate system. In other examples the feet first or head first orientation may be determined relative to a coordinate system of a radiotherapy system, a direction towards the radiotherapy system, or determined relative to a motion direction of a subject support to transport a subject within or to a radiotherapy system.

Determining if the subject is in a decubitus pose, a supine pose, or a prone pose can be a difficult task. In a decubitus pose the subject is on his or her side and the decubitus pose can sometimes be partially prone or supine. To make this determination, embodiments use the location of the left hip joint, the right hip joint, the right shoulder joint, and the left shoulder joint.

A torso aspect ratio can be calculated. The location of the left hip joint, the right hip joint, the right shoulder joint, and the left shoulder joint define a quadrilateral. The long sides of the quadrilateral are defined by the left hip joint to the left shoulder joint and/or the right hip joint to the right shoulder joint. The short sides of the quadrilateral are defied by the left hip joint to the right hip joint and/or the right shoulder joint to the left shoulder joint. The torso aspect ratio is the ratio of the length of long side(s) of the quadrilateral to the length of the short side(s) of the quadrilateral. For the length of the long side, the length of the left hip joint to the left shoulder joint, the length of the right hip joint to the right shoulder joint, or an average of the two may be used. For the length of the short side, the length of the left hip joint to the right hip joint, the length of the right shoulder joint to the left shoulder joint, or an average of the two may be used.

If the torso aspect ratio is above a predetermined threshold, then the subject is determined to be in the decubitus pose. If either hip or shoulder left and right part location probabilities are overlapping and thus the ratio starts to diverge this would correspond to a strict decubitus pose. If the subject is less than or equal to the predetermined threshold then the subject is in a supine pose or a prone pose. The predetermined logic module can be programmed to take as input the set of joint location coordinates and output if the subject is face down or face up on the subject support.

In tests using the golden ratio (or golden section) as the predetermined threshold was effective. In this case the predetermined threshold would be approximately 1.6. In some examples the predetermined threshold could be between 1.5 and 1.8.

In one aspect the invention provides for a medical instrument that comprises a memory storing machine-executable instructions. The medical instrument further comprises a processor configured to control the medical instrument.

Depending upon the configuration of the medical instrument the processor may provide different types of control. In some examples, the medical instrument is a computer workstation or remote system available via the internet or as a cloud service. In this case the control of the medical instrument is the providing of computational, numerical, and/or image processing tasks. In other examples, the medical instrument may comprise additional components such as a camera system and/or radiotherapy system. In this case control of the medical instrument by the processor include the control of these additional components.

Execution of the machine-executable instructions causes the processor to receive a set of joint location coordinates for a subject reposing on a subject support. A subject such as a human has bones that are connected by joints. The joint location coordinates indicate the position of the joints of the skeletal system of a subject. Typically, only the major joints are indicated. The set of joint location coordinates comprises coordinates for a left hip joint, a right hip joint, a right shoulder joint, and a left shoulder joint.

Execution of the machine-executable instructions further causes the processor to identify a body orientation by inputting the set of joint locations into a predetermined logic module. The body orientation is head first or feet first. The identification of the body orientation with the predetermined logic module may be achieved by a knowledge that some joints are closer to the head or the feet than other joints. For example, the right shoulder joint is closer to the head of the subject than the right hip joint. A knowledge of where the right hip joint and the right shoulder joint then indicates whether the body orientation is head first or feet first. This for example can be achieved by using different combinations of different joint location coordinates.

As used herein face up and face down refer to the orientation of the subjects torso. When the subject is face up on the subject support the subject's back rests on the subject support. When the subject is face down on the subject support, the subject's chest rests on the subject support.

In one example if a subject is observed from above, a point can be chosen that is between the left shoulder joint, the right shoulder joint, the left hip and the right hip joint. If one rotates about this point the right shoulder joint will always be clockwise from the left shoulder joint (as observed from above). Likewise, the left shoulder joint will always be clockwise from the right shoulder joint (as observed from above).

A variety of other logical conditions similar to these two can also be constructed. In fact, an equivalent predetermined logic can be used to determine if the subject is face up or face down by choosing any three of the left shoulder joint, the right shoulder joint, the left hip joint, and the right hip joint and applying logic. Using three of the predetermined logic module in some cases may be easier, because three points automatically defines a plane in which the three chosen joints can be rotated.

As a concrete example, the left shoulder joint, the right shoulder joint, and the right hip joint are used. These three points define a triangle on a plane. If a central point such as a centroid of the triangle is taken, when the subject is face down, as observed from above, the right shoulder joint is always adjacent to and clockwise when coming from the left shoulder joint, the right hip joint is always adjacent to and clockwise when coming from the right shoulder joint. The left shoulder joint is always adjacent to and clockwise when coming from the right hip joint. It is clear from this example that there are many variations on this which could be used to provide the logical conditions for a predetermined logic module.

Execution of the machine-executable instructions further causes the processor to calculate a torso aspect ratio from the location of the left hip joint, the right hip joint, the right shoulder joint, and the left shoulder joint. These four joint location coordinates define a quadrilateral. The torso aspect ratio can for example be calculated as describe above.

Execution of the machine-executable instructions further causes the processor to determine if the torso aspect ratio is greater than a predetermined threshold. If this is the case then the body pose of the subject is identified as being a decubitus pose. This is a pose where the subject is on the right or left side. Execution of the machine-executable instructions further cause the processor to determine if the aspect ratio is less than or equal to the predetermined threshold and then identify if the body pose of the subject is face up or face down. If the position of the subject is face down then the body orientation is identified as being a prone pose. If the orientation of the subject is identified as being face up then the body orientation is defined as being a supine pose.

The identification of the subject being face up or face down may again be determined using the predetermined logic module. With a knowledge if the subject is feet first or head first the position of individual joint location coordi-nates can be used to determine if the subject is face down or face up. This then defines whether the subject is in the prone or supine pose. Execution of the machine-executable instructions further cause the processor to generate a subject pose label from at least the body orientation and the body pose. The subject pose label may for example be useful in control systems for the medical instrument for controlling imaging and radiotherapy applications as well as labeling medical images acquired with medical imaging systems. The use of the torso aspect ratio to determine if the subject is in a decubitus pose or not may be useful because often times subjects are not completely on their back or on their side. This provides an efficient means of discriminating the various poses.

In another embodiment the set of joint location coordinates comprises a left knee joint, a right knee joint and a neck joint. The left knee joint coordinate comprises a left knee joint angle with the first restricted angle of motion; the right knee joint comprises a right knee joint with a second restricted range of motion. The neck joint comprises a neck joint angle with a third restricted range of motion. These three joints are only able to move within a finite range of angles. These limitations are constraints which may be used to identify the position of the subject. The decubitus pose is classified as being a left decubitus pose or a right decubitus pose by inputting the first restricted range of motion, the second restricted range of motion, and the third restricted range of motion into the predetermined logic module. Having a knowledge of the possible angles that a joint can assume for a subject within the left or right decubitus pose enables a knowledge of these restricted range of motion angles to determine if the subject is in the left decubitus or right decubitus pose.

In another embodiment, execution of the machine executable instructions further causes the processor to calculate a decubitus pose measure from a difference between the predetermined threshold and the torso aspect ratio. The subject pose label further comprises decubitus pose measure. For example, the difference between predetermined thresholds may be input into an algorithm which returns a number which indicates how close the subject's pose is to a decubitus pose. This may be useful to know if the subject is having trouble assuming a decubitus pose.

In another embodiment, the memory further contains a joint locator module configured to construct the set of joint location coordinates in response to receiving an image of the subject on the subject support. Execution of the machine executable instructions further causes the processor to: receive the image of the subject on the subject support and receive the set of joint location coordinates in response to inputting the image into the joint locator module.

In another embodiment the memory further contains a neural network configured to output a separate joint location probability map for each of the set of joint location coordinates in response to receiving an image of the subject on the subject support. Execution of the machine-executable instructions causes the processor to receive the image of the subject on the subject support. Execution of the machine-executable instructions further causes the processor to receive the separate joint location probability map for each of the set of joint locations by inputting the image into the neural network. Execution of the machine-executable instructions further causes the processor to calculate the set of joint location coordinates from the separate joint location probability map for each of the set of joint locations.

When a subject is located on a subject support it may be extremely difficult to determine the location of individual joints. The neural network is not used to provide specific coordinates. Instead each of the set of joint location coordinates has its own probability map that is output. The probability maps may then be used to determine the joint locations. For example, the voxel or pixel with the highest value may be chosen as the joint location. In other examples the overall distribution may be examined and the centroid or the average or the mean location may be chosen instead. This may provide for a more robust means of identifying the locations of the joints of a subject.

In another embodiment the probability map for each of the set of joint locations has the same dimension in pixels as the image of the subject on the subject support. This may be beneficial in identifying the location of the joints of the subject in the image.

In another embodiment the medical instrument comprises a camera. Execution of the machine-executable instructions further causes the camera to acquire the image of the subject on the subject support.

In another embodiment execution of the machine-executable instructions further causes the processor to train the neural network with a set of labeled images. The labeled images may for example contain images of subjects with the location of the various joints indicated in an image. The set of labeled images comprises images of the subjects reposed on the subject support, front views of subjects, rear views of subjects, empty subject supports, subject supports containing medical equipment, and partially obscured images of subjects. This combined with the generation of the separate joint location probability map for each joint may result in a system that identifies the set of joint location coordinates better than existing systems.

In another embodiment the medical instrument further comprises a medical imaging system configured for acquiring medical imaging data from an imaging zone. The subject support is configured for at least partially supporting the subject within the imaging zone. The label of feet first may indicate that the feet first enter the imaging zone when the subject is moved to within the imaging zone. Likewise, the label of head first indicates that the head region of the subject first moves into the imaging zone when the subject is moved into the imaging zone.

In another embodiment the medical imaging system is a magnetic resonance imaging system.

In another embodiment the medical imaging system is a positron emission tomography system.

In another embodiment the medical imaging system is a single photon emission tomography system.

In another embodiment the medical imaging system is a digital X-ray system.

In another embodiment the medical imaging system is a computed tomography or CT system.

In another embodiment the memory further comprises a medical imaging protocol. The medical imaging protocol may for example contain instructions or commands which can be converted into instructions which may be used for controlling the medical imaging system to acquire medical imaging data. The medical imaging protocol comprises a selected pose label. Execution of the machine-executable instructions further cause the processor to perform any one of the following if the subject pose label differs from the selected pose label: provide a warning signal, select a different medical imaging protocol matching that comprises the subject pose label, provide instructions on repositioning the subject, and combinations thereof. This embodiment may be beneficial because it may prevent the subject from being imaged improperly in the medical imaging system.

In another embodiment execution of the machine-executable instructions further causes the processor to control the medical imaging system to acquire medical imaging data. This for example may be accomplished using commands or instructions contained within the medical imaging protocol. Execution of the machine-executable instructions further causes the processor to create an image file comprising the medical imaging data and the subject pose label. For example, the image file may be a DICOM image. Execution of the machine-executable instructions further causes the processor to store the image file in a picture archiving and communication system. This embodiment may be beneficial because it ensures that the position of the subject is stored with the acquired medical imaging data.

In another embodiment the medical instrument further comprises a radiotherapy system configured for eradiating targets within an eradiation zone. The subject support is configured to support the subject at least partially within the eradiation zone. The addition of such an eradiation zone may be beneficial because the subject pose of the subject during radiotherapy is critical for proper treatment.

In another embodiment the memory further comprises a radiotherapy protocol. The radiotherapy protocol comprises a selected pose label. Execution of the machine-executable instructions further causes the processor to perform any one of the following if the subject pose label differs from the selected pose label: provide a warning signal, halt execution of the radiotherapy protocol, provide instructions on repositioning the subject, and combinations thereof. This embodiment may be beneficial because it may prevent the subject from being eradiated improperly.

In another embodiment the set of joint location coordinates further comprises: a left elbow joint coordinate and a right elbow joint coordinate. The left elbow joint coordinate comprises a left elbow joint angle. The right elbow joint comprises a right elbow joint angle. The left shoulder joint coordinate comprises a left shoulder joint angle. The right shoulder joint coordinate comprises a right shoulder joint angle.

Execution of the machine-executable instructions further causes the processor to determine an arm position classification by inputting the right shoulder joint angle, the left shoulder joint angle, the right elbow joint angle, and the left elbow joint angle into the predetermined logic module. The arms of a subject can only bend in certain directions as defined by the elbows and the shoulders. The predetermined logic module can therefore be programmed to use this information to determine the arm position classification. Execution of the machine-executable instructions further causes the processor to append the arm position classification to the subject pose label. This may be beneficial because it may provide greater detail on the position of the subject during radiotherapy or imaging.

In another aspect the invention provides for a method of medical imaging. The method comprises receiving a set of joint location coordinates from a subject reposing on a subject support. The set of joint location coordinates comprises coordinates for: a left hip joint, a right hip joint, a right shoulder joint, and a left shoulder joint. The method further comprises identifying a body orientation by inputting the set of joint locations into a predetermined logic module. The body orientation is head first or feet first. The method further comprises calculating a torso aspect ratio from the location of the left hip joint, the right hip joint, the right shoulder joint, and the left shoulder joint. The method further comprises identifying a body pose of the subject as being a decubitus pose if the torso aspect ratio is below a predetermined threshold.

The method further comprises identifying the body pose of the subject as being a prone pose if the torso aspect ratio is above the predetermined threshold and the body orientation is that the subject is positioned face up on the subject support according to the predetermined logic module. The predetermined logic module in this case will take the set of joint location coordinates as input.

The method further comprises determining that the body pose of the subject is a supine pose if the torso aspect ratio is above the predetermined threshold as well as the predetermined logic module determining that the subject is face down. This for example may be achieved by inputting the set of joint location coordinates into the predetermined logic module. The method further comprises generating a subject pose label from at least the body orientation and the body pose.

In another aspect the invention provides for a computer program product comprising machine-executable instructions for execution by a processor controlling a medical instrument. Execution of the machine-executable instructions further causes the processor to receive a set of joint location coordinates for a subject reposing on a subject support. The set of joint location coordinates comprises coordinates for a left hip joint, a right hip joint, a right shoulder joint, and a left shoulder joint. Execution of the machine-executable instructions further causes the processor to identify a body orientation by inputting the set of joint locations into a predetermined logic module. The body orientation is either head first or feet first.

Execution of the machine-executable instructions further causes the processor to calculate a torso aspect ratio from the location of the left hip joint, the right hip joint, the right shoulder joint, and the left shoulder joint. Execution of the machine-executable instructions further causes the processor to determine that the body pose of the subject is a decubitus pose if the torso aspect ratio is greater than a predetermined threshold.

Execution of the machine-executable instructions further causes the processor to determine that the body pose of the subject is a prone pose if the aspect ratio is less than or equal to the predetermined threshold as well as the predetermined logic module determining that the subject is face down. The set of joint location coordinates may be input into the predetermined logic module to determine this.

Execution of the machine-executable instructions further causes the processor to determine that the body pose of the subject is a supine pose if the aspect ratio is less than or equal to the predetermined threshold as well as the predetermined logic module determining that the subject is face up. The set of joint location coordinates may be input into the predetermined logic module to determine this. Execution of the machine-executable instructions further causes the processor to generate a subject pose label from at least the body orientation and the body pose.

In another aspect the method is implemented as machine executable instructions or code for execution by a processor controlling a medical instrument.

It is understood that one or more of the aforementioned embodiments of the invention may be combined as long as the combined embodiments are not mutually exclusive.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example, a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems.

The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances, the computer executable code may be in the form of a high-level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It is understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, pedals, wired glove, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Magnetic Resonance (MR) data is defined herein as being the recorded measurements of radio frequency signals emitted by atomic spins using the antenna of a Magnetic resonance apparatus during a magnetic resonance imaging scan. Magnetic resonance data is an example of medical image data. A Magnetic Resonance Imaging (MM) image or MR image is defined herein as being the reconstructed two- or three-dimensional visualization of anatomic data contained within the magnetic resonance imaging data. This visualization can be performed using a computer.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
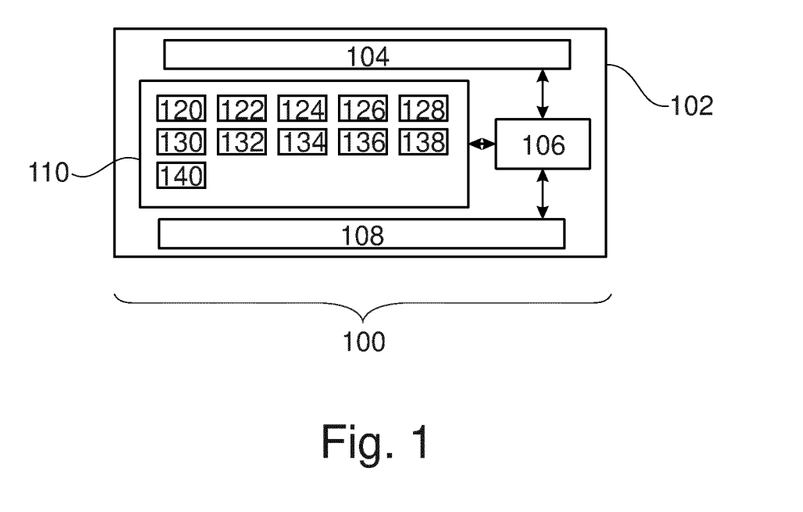
FIG. 1 illustrates an example of a medical instrument.

FIG. 1 illustrates an example of a medical instrument 100. The medical instrument 100 in FIG. 1 comprises a computer 102. The computer 102 comprises a hardware or network interface 104 that is useful for connecting to other components of the medical instrument and/or for networking with other computer systems. The computer 102 is further shown as containing a processor 106. The processor is also connected to the hardware or network interface 104. Additionally, there is a memory 110 and an optional user interface 108 that are also connected to the processor.

The memory 110 is shown as containing machine-executable instructions 120 that enable the processor 106 to control the operation and function of the medical instrument 100 as well as perform various data and imaging processing tasks. The memory 110 is further shown as containing an image of the subject 122. The image of the subject 122 may be optional in some examples. The memory 110 is further shown as containing a neural network 124 that is configured for receiving the image of the subject 122 and outputting joint location probability maps 126 for every member of a set of joint location coordinates 128. The neural network 124 and the joint location probability maps 126 may be optional in some examples. The joint location probability maps 126 are individual probability maps that each contain the probability of the location of a particular joint of the subject.

The joint location probability maps 126 may be processed to derive or generate a set of joint location coordinates 128. The memory 110 is further shown as containing a predetermined logic module 130. The set of joint location coordinates 128 are a defined location of the subject. By using predetermined logic, the information contained in the set of joint location coordinates 128 can be used to derive properties of the subject; for example, the location of the head relative to the foot. Additionally, this information can be used to determine if the subject is face up or face down on the subject support. Various joints of the subject have a limited range of motion. This limited range of motion can also be useful for inferring the position or orientation of the subject. For example, knee and elbow joints only bend in a certain direction within a predetermined range for subjects. The determination of the angle of a particular knee or elbow joint can for example be used to determine the way a subject is lying or even the arm position.

The memory 110 is further shown as containing a body orientation 132 that indicates whether the subject is head first or feet first on the subject support. This may be determined by inputting the set of joint location coordinates 128 into the predetermined logic module 130. The memory 110 is further shown as containing a torso aspect ratio. The torso aspect ratio was described previously as being determined by the location of the hip and shoulder joints. The torso aspect ratio 134 can be compared to a predetermined threshold 136. This for example may be equal to the golden mean in some examples. If the torso aspect ratio 134 is below this predetermined threshold 136 the body pose 138 can be inferred as being a decubitus pose in some examples. If the torso aspect ratio 134 is above the predetermined threshold 136 then the body pose is supine or prone.

The predetermined logic module 130 can be used to determine if the subject is face up or face down. The body pose can then be determined to be in the supine or prone pose using the predetermined logic module 130. The angles of the knee in a healthy or normal subject can only bend within a particular angular range. The angles of the knee joints may therefore for example be useful in determining if the subject is in a left or right decubitus pose. The shoulder and the elbow joints also bend within a predetermined range. The predetermined logic module 130 can also be used to determine an arm position classification 140. This may be optional in some examples. The memory 142 is then also shown as containing a subject pose label 142 that was determined by the body pose 138, the optional arm classification 140 and the body orientation 132.

Figure 2:
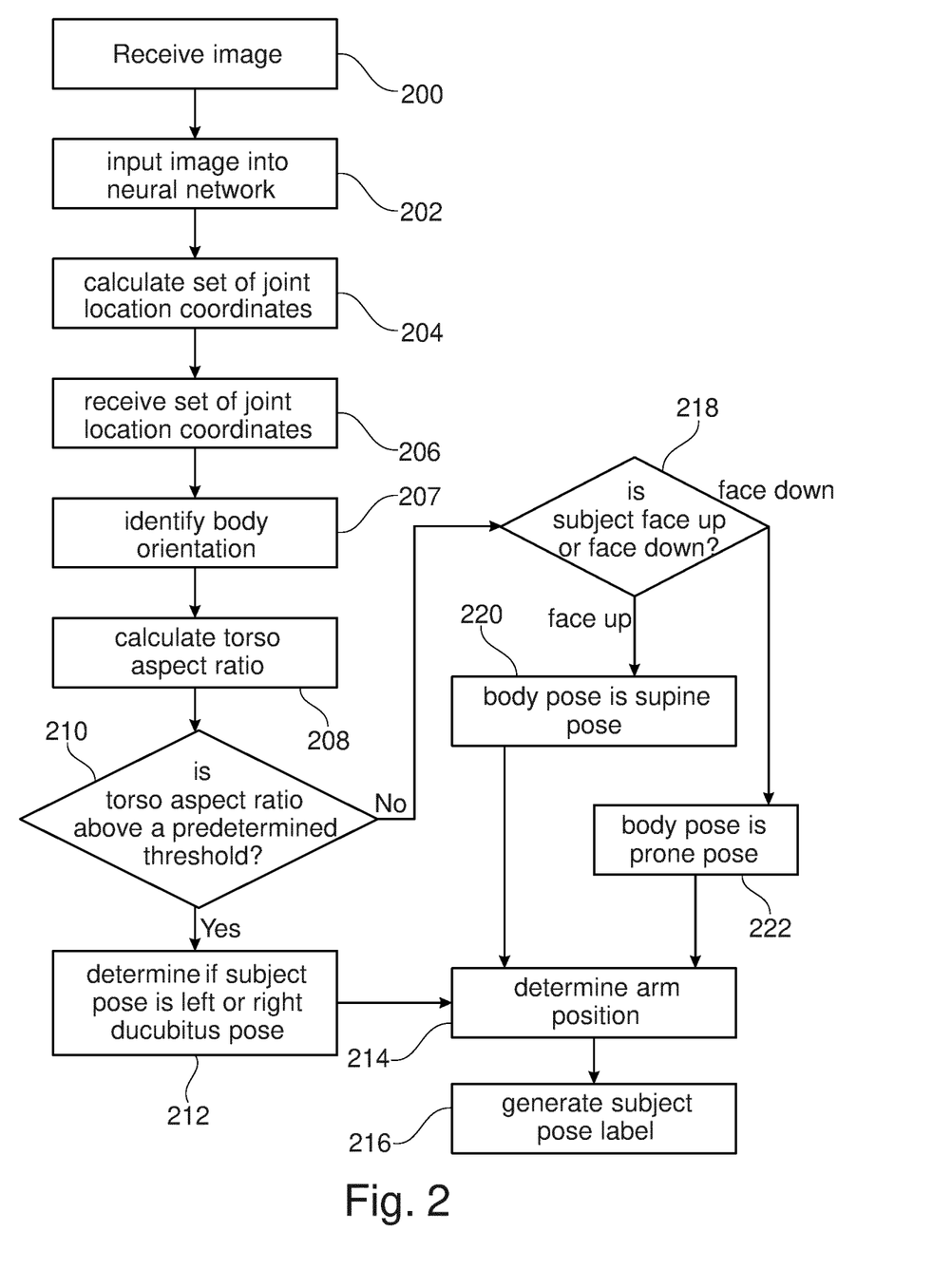
FIG. 2 shows a flow chart which illustrates a method of operating the medical instrument of FIG. 1.

FIG. 2 shows a flowchart which illustrates a method of operating the medical instrument 100 of FIG. 1. First in step 200 the image 122 of the subject on the subject support is received. Next in step 202 the joint location probability maps 126 are received by inputting the image 122 into the neural network 124. Then in step 204 the set of joint location coordinates 128 are calculated from the joint location probability maps 126. As was mentioned previously, a different statistical analysis may be applied to the distributions displayed in the joint location probability maps 126 to calculate the set of joint location coordinates 128. Then in step 206 the set of joint location coordinates 126 is received. Next in step 207, the body orientation 132 is identified by inputting the set of joint location coordinates 128 into the predetermined logic module 130. In step 208 the torso aspect ratio 134 is calculated from the location of the left hip joint, the right hip joint, the right shoulder joint, and the left shoulder joint.

The method then proceeds to box 210. In 210 is the question, is the torso aspect ratio above a predetermined threshold. If the answer is yes then the subject is in a decubitus pose and the method proceeds to step 212. In step 212 it is determined is the subject in a left or right decubitus pose. This may be accomplished by inputting the set of joint location coordinates 128 into the predetermined logic module 130. Next the method proceeds to step 214. Step 214 is optional in some examples. In step 214 the arm position classification 140 is determined by inputting the set of joint location coordinates 128 into the predetermined logic module 130. After step 214 is performed the method proceeds to step 216. In step 216 the subject pose label 142 is generated from the body orientation 132 and at least the body pose 138. In some examples the arm position classification 140 is also used in generation of the subject pose label 142.

Returning to step 210, if the answer to the question is no then the method proceeds to step 218. Step 218 is a different decision box and the question is is the subject face up or face down. The answer to this question may be obtained as was described earlier, by inputting the set of joint location coordinates 128 into the predetermined logic module 130. If the answer is face up then the method proceeds to step 220 and the body pose is identified as being a supine pose. If the answer is face down the method proceeds to step 222 and the body pose is identified as being a prone pose. After step 220 or 222 is performed the method proceeds again to step 214 and then step 216 as previously described.

Figure 3:
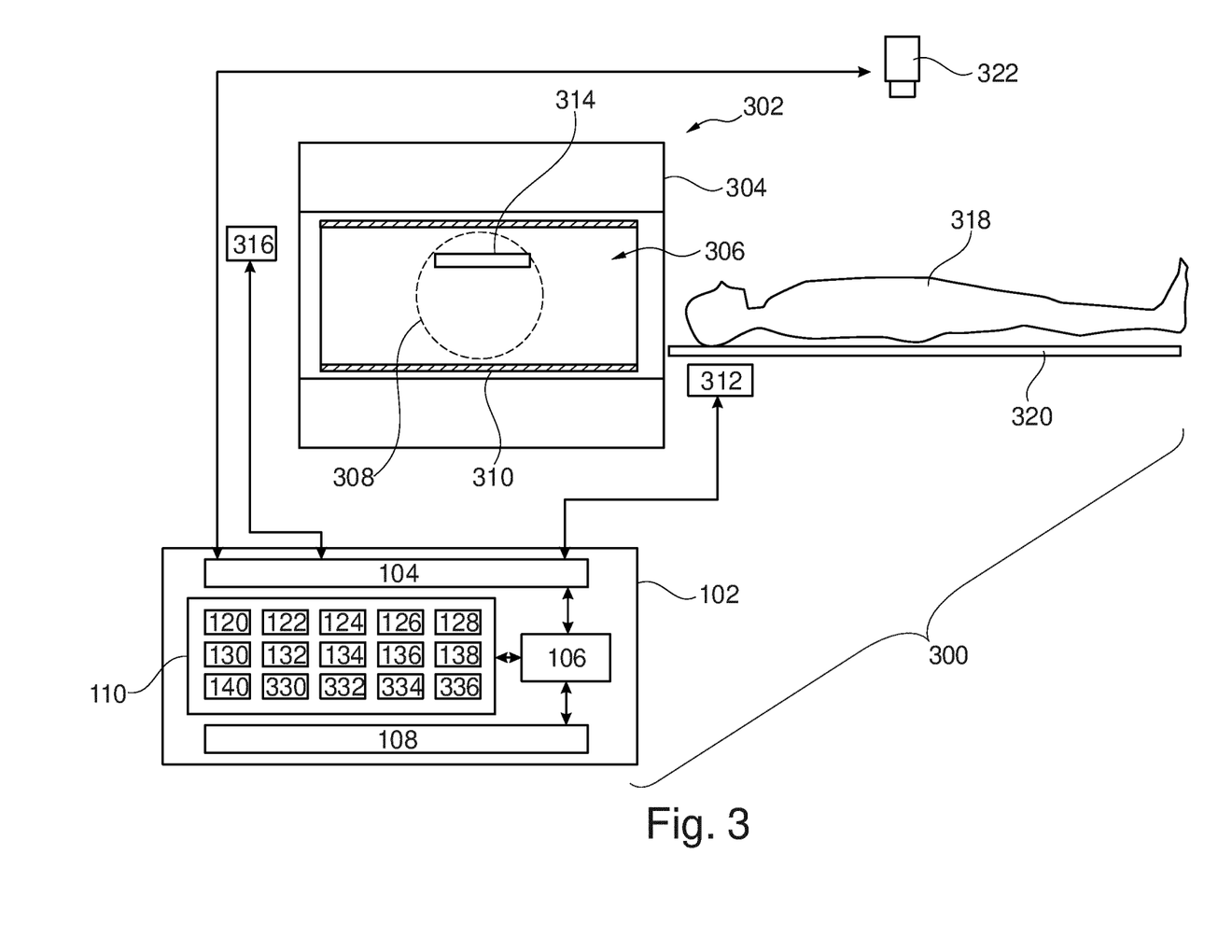
FIG. 3 illustrates a further example of a medical instrument.

FIG. 3 illustrates a further example of a medical system 300. The medical system 300 in FIG. 3 is similar to the medical system 100 in FIG. 1 except that the medical system additionally comprises a magnetic resonance imaging system 302.

The magnetic resonance imaging system 302 comprises a magnet 304. The magnet 304 is a superconducting cylindrical type magnet with a bore 306 through it. The use of different types of magnets is also possible; for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils.

Within the bore 306 of the cylindrical magnet 304 there is an imaging zone 308 where the magnetic field is strong and uniform enough to perform magnetic resonance imaging. The magnetic resonance data that is acquired typically acquired for the field of view. A subject 318 is shown as being supported by a subject support 320 in view of a camera 322.

The camera 322 is shown as being position so that the subject 318 can be imaged when reposing on the subject support 320. In this example the subject 318 is positioned head first. The subject's head will enter the bore 306 of the magnet 304 first when the subject support 320 is used to move the subject 318 into the imaging zone 308.

Within the bore 306 of the magnet there is also a set of magnetic field gradient coils 310 which is used for acquisition of preliminary magnetic resonance data to spatially encode magnetic spins within the imaging zone 508 of the magnet 504. The magnetic field gradient coils 310 connected to a magnetic field gradient coil power supply 312. The magnetic field gradient coils 310 are intended to be representative. Typically magnetic field gradient coils 310 contain three separate sets of coils for spatially encoding in three orthogonal spatial directions. A magnetic field gradient power supply supplies current to the magnetic field gradient coils. The current supplied to the magnetic field gradient coils 310 is controlled as a function of time and may be ramped or pulsed.

Adjacent to the imaging zone 308 is a radio-frequency coil 314 for manipulating the orientations of magnetic spins within the imaging zone 308 and for receiving radio transmissions from spins also within the imaging zone 308. The radio frequency antenna may contain multiple coil elements. The radio frequency antenna may also be referred to as a channel or antenna. The radio-frequency coil 314 is connected to a radio frequency transceiver 316. The radio-frequency coil 314 and radio frequency transceiver 316 may be replaced by separate transmit and receive coils and a separate transmitter and receiver. It is understood that the radio-frequency coil 314 and the radio frequency transceiver 316 are representative. The radio-frequency coil 314 is intended to also represent a dedicated transmit antenna and a dedicated receive antenna. Likewise the transceiver 316 may also represent a separate transmitter and receivers. The radio-frequency coil 314 may also have multiple receive/transmit elements and the radio frequency transceiver 316 may have multiple receive/transmit channels. For example if a parallel imaging technique such as SENSE is performed, the radio-frequency could 314 will have multiple coil elements.

The transceiver 316 and the gradient controller 312 are shown as being connected to the hardware interface 104 of the computer system 102.

The memory 110 is further shown as containing pulse sequence commands 330. The pulse sequence commands could for example contain a label which may be compared to the subject pose label 142. This may be used as a quality control check. In this example the pulse sequence commands 330 may be considered to be a protocol. The memory 110 is further shown as containing magnetic resonance data 332 that was acquired by controlling the magnetic resonance imaging system 302 with the pulse sequence commands 330. The memory 110 is further shown as containing a magnetic resonance image 334 that was reconstructed from the magnetic resonance data 332. The memory 110 is further shown as containing a DICOM image 336 that was constructed from the magnetic resonance image 334 and also stores the subject pose label 142.

Figure 4:
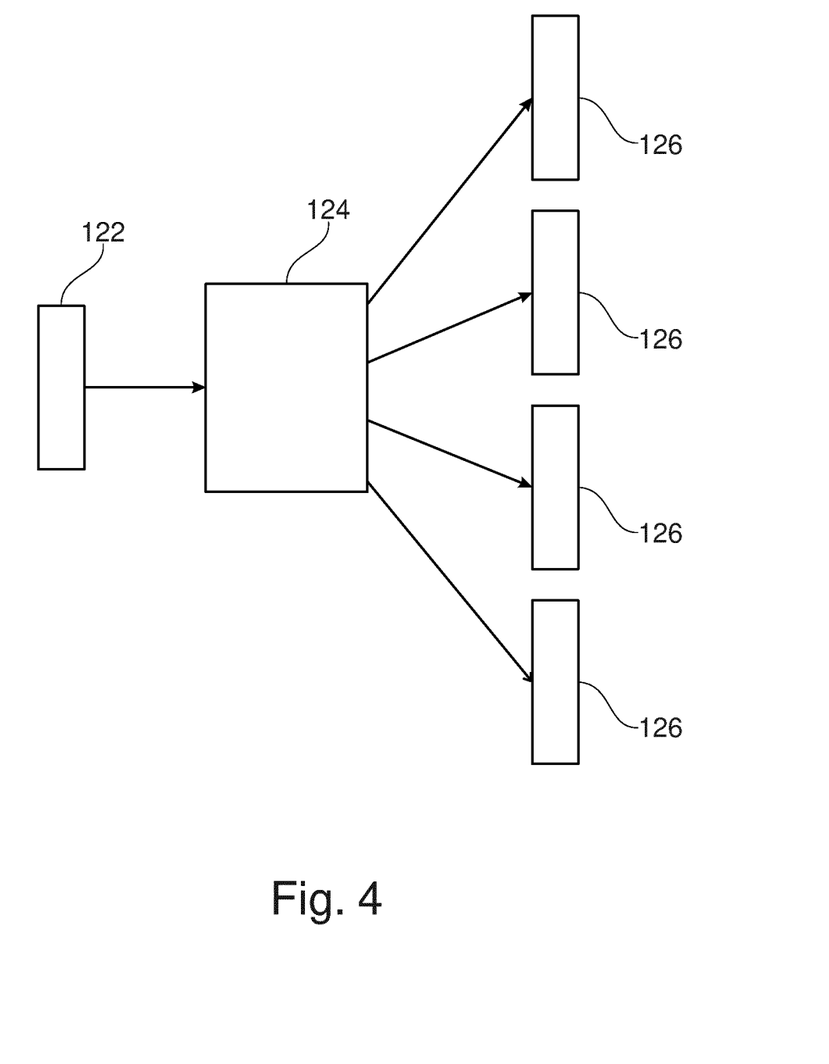
FIG. 4 illustrates an example of a neural network.

FIG. 4 illustrates the operation of the neural network 124. An image of the subject 122 is shown as being input into the neural network 124. The neural network 124 in response outputs a number of joint location probability maps 126. The number of joint location probability maps 126 will match the number of elements in the set of joint location coordinates 128.

For an MR or CT examination proper patient position and orientation is preferably entered by the tech to ensure correct patient coordinate system for diagnosis, e.g. to ensure correct laterality of anatomy for diagnosis. Setting up the patient is a dynamic process depending on the compliance level of the patient. Therefore, deviations of the actual vs. the prescribed patient position and orientation are common and require attention of the tech to not forget the respective changes in the examination protocol. Failures to do so can have severe consequences for diagnosis and the responsible tech. Detecting the actual patient position and orientation automatically is therefore of particular interest. Camera images can be used for this. Classification of the poses from such images using neural networks is challenging due to the amount of labelled data that is necessary. Definition of pose classes is sometimes difficult for intermediate poses. Also extending the pose classes is challenging.

Examples may perform the classification of the pose using the position of body joint positions (joint location coordinates 128). Body joints represent the motion degrees of freedom of the human body. Such body joint positions allow to calculate joint angles and apparent projected body proportions. The example may use any of the following predetermined logic:

Determine relative position of upper body joints with respect to lower body joints
Derive patient head-first vs. feet-first probability
Calculate apparent torso proportions and determine deviation from a predetermined threshold 136. The golden section may be used as the predetermined threshold.
The degree of deviation from the predetermined threshold (i.e. golden section) gives degree of decubitus pose
If decubitus pose: Determine side using knee, hip and neck angles (angles with natural movement limitation)

If non-decubitus: Decide supine vs. prone based on shoulder sides and hip sides positions Determine arm up or down pose based on shoulder angle All thresholds can be adapted and poses can be determined including Head-first supine/prone, decubitus left/right, left/right arm up/down.

The algorithm functions using a normal camera image, i.e. 3D information is not required. If 3D information is available it could be used for cross checks. However, it was found that the combination of joint angles and body proportions provides more robust markers to derive the patient pose. Since all important joints can be localized, the pose classes can be extended and can be adapted to the requirements of the modalities. Also transition classes are possible: E.g. the algorithm allows classes like: 65% Prone/35% Left Decubitus which may be useful for more precise positioning of the patient e.g. for radiotherapy applications.

Figure 5:
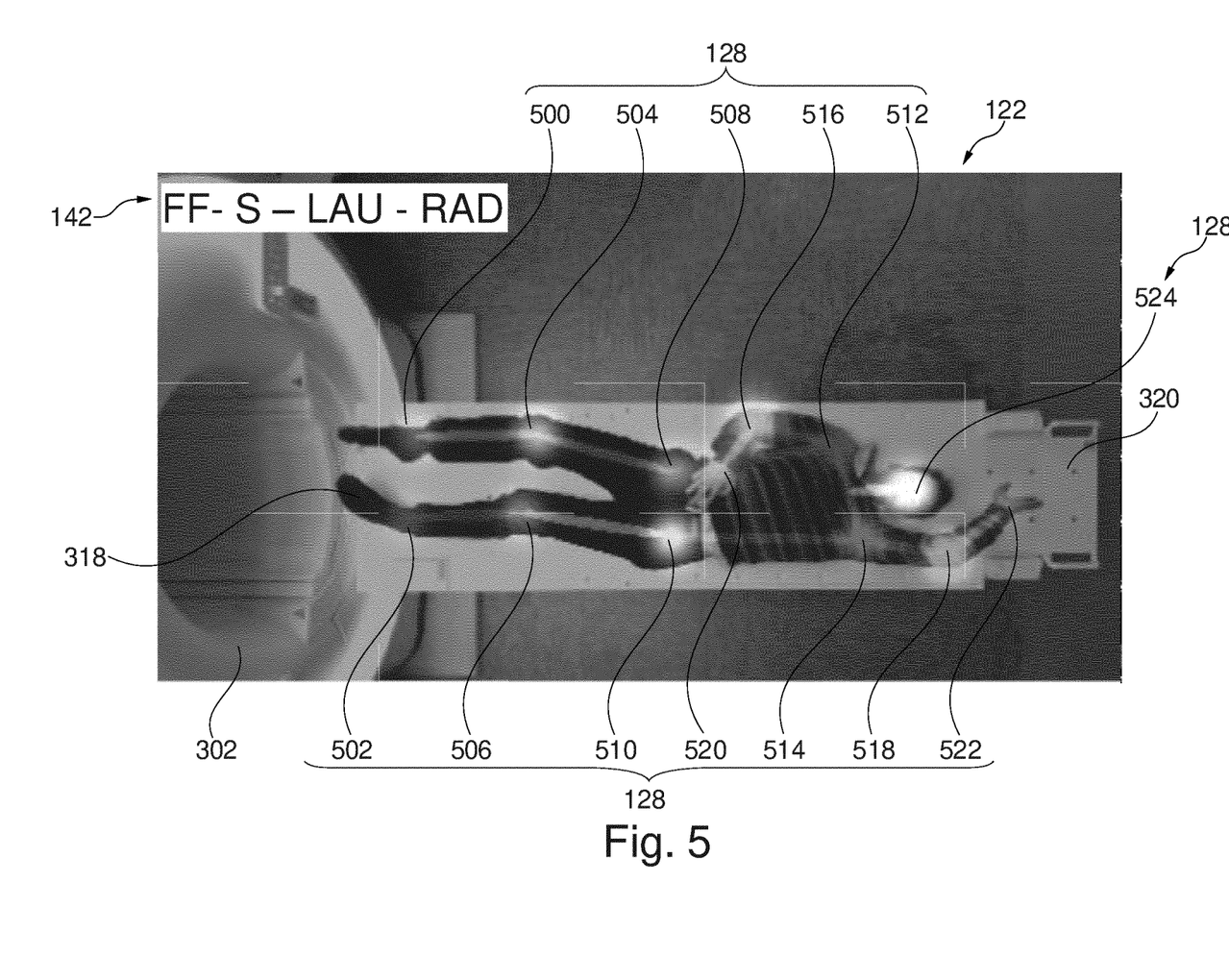
FIG. 5 shows an example of an image of a subject superimposed with a set of joint location coordinates.

FIG. 5 illustrates an example of an image 122 of the subject 318 on the subject support 320. The subject is in a feet first pose. The feet will enter the magnetic resonance imaging system first. Additionally, the subject is in a supine pose and is face up. The subject's right arm is folded across the chest and the left arm is raised above the head. The joint angle coordinates are also labeled. The right ankle joint coordinate 500, the left ankle joint coordinate 502, the right knee joint coordinate 504, the left knee joint coordinate 506, the right hip joint coordinate 508, the left hip joint coordinate 510, the right shoulder joint coordinate 512, the left shoulder joint coordinate 514, the right elbow joint coordinate 516, the left elbow joint coordinate 518, the right wrist joint coordinate 520, the left wrist joint coordinate 522 and the neck joint coordinate 524 are all visible. The label for this position is labeled 142. The label is: feet first (FF), supine (S), left arm up (LAU), and right arm down (RAD). FIG. 5 shows a typical supine pose feet-first. Here the apparent torso proportion is very close to the golden ratio.

Figure 6:
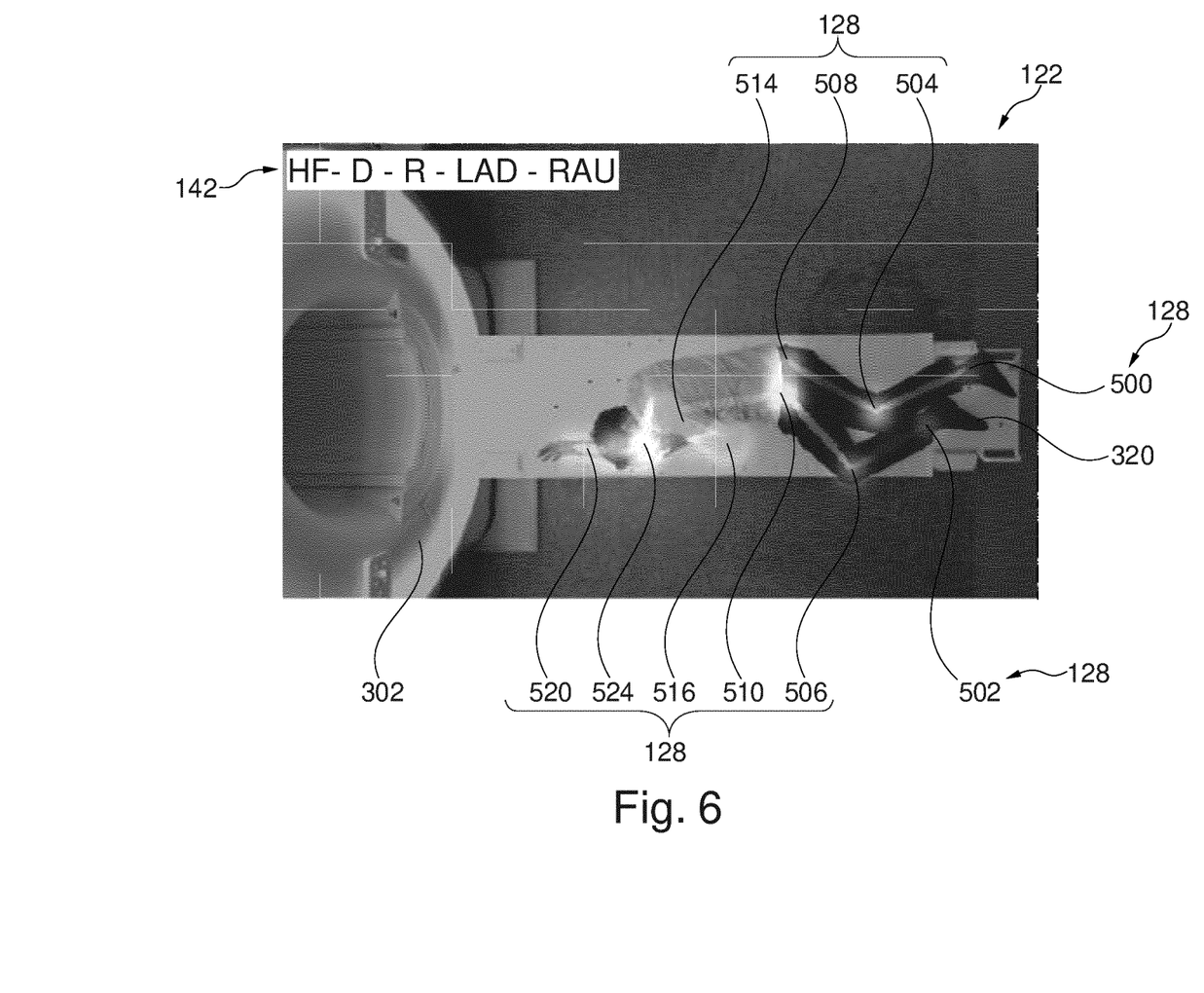
FIG. 6 shows a further example of an image of a subject superimposed with a set of joint location coordinates.

FIG. 6 illustrates another example of an image 122 of the subject on the subject support. In this example the subject is in a decubitus pose. It can be seen how the angles around the knee joints 504, 506 can be used to determine in which direction the subject is turned to. The label 142 is: decubitus pose (D) right (R), left arm down (LAD), and right arm up (RAU). FIG. 6 illustrates the typical knee, hip and neck angles for a decubitus pose. The pose was successfully classified as Head-first, decubitus left, left arm down, right arm up. Note the apparent torso proportions, i.e. the ratio between shoulder-hip-distance/shoulder-span (and/or hip-span)

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 medical instrument
102 computer
104 hardware or network interface
106 processor
108 user interface
110 memory
120 machine executable instructions
122 image of the subject (optional)
124 neural network
126 joint location probability maps
128 set of joint location coordinates
130 predetermined logic module
132 body orientation (head or feet first)
134 torso aspect ratio
136 predetermined threshold
138 body pose
140 arm position classification (optional)
142 subject pose label
200 receive the image of the subject on the subject support
202 receive the separate joint location probability map in response to inputting the image into the neural network
204 calculate the set of joint location coordinates from the separate joint location probability map for each of the set of joint locations
206 receive a set of joint location coordinates for a subject reposing on a subject support
207 receive a body orientation in response to inputting the set of joint location coordinates into a predetermined logic module
208 calculate a torso aspect ratio from the location of the left hip joint, the right hip join, the right shoulder joint, and the left shoulder joint
210 Is the torso aspect ratio above a predetermined threshold?
212 assign the decubitus pose to the body pose
214 determine the arm position
216 generate a subject pose label
218 Is the subject face up or face down on the subject support?
220 the body pose is a supine pose
222 the body pose is a prone pose
300 medical system
302 magnetic resonance imaging system
304 magnet
306 bore of magnet
308 imaging zone
309 field of view
310 magnetic field gradient coils
312 magnetic field gradient coil power supply
314 radio-frequency coil
316 transceiver
318 subject
320 subject support
322 camera
330 pulse sequence commands
332 magnetic resonance data
334 magnetic resonance image
336 dicom image
500 right ankle joint coordinate
502 left ankle joint coordinate 504 right knee joint coordinate
506 left knee joint coordinate
508 right hip joint coordinate
510 left hip joint coordinate
512 right shoulder joint coordinate
514 left shoulder joint coordinate
516 right elbow joint coordinate
518 left elbow joint coordinate
520 right wrist joint coordinate
522 left wrist joint coordinate
524 neck joint coordinate

The invention claimed is:

1. A medical instrument comprising:
a memory configured to store machine executable instructions and a predetermined logic module; and
a processor configured to control the medical instrument, wherein execution of the machine executable instructions causes the processor to:
receive a set of joint location coordinates for a subject reposing on a subject support-; wherein the set of joint location coordinates comprises coordinates for: a left hip joint, a right hip joint, a right shoulder joint, and a left shoulder joint;
receive a body orientation in response to inputting the set of joint location coordinates into a predetermined logic module, wherein the body orientation is head first or feet first relative to a chosen coordinate system;
calculate a torso aspect ratio from the location of the left hip joint, the right hip joint, the right shoulder joint, and the left shoulder joint;
wherein if the torso aspect ratio is greater than a predetermined threshold then assign a body pose of the subject as being a decubitus pose;
wherein if the torso aspect ratio is less than or equal to the predetermined threshold receive a determination if the subject is face up or face down on the subject support in response to inputting the set of joint location coordinates into the predetermined logic model, wherein face up and face down are an orientation of a torso of the subject, wherein if the subject is face up a back of the subject rests on the subject support, wherein if the subject is face down a chest of the subject rests on the subject support;
assign the body pose as being a supine pose if the subject is face up on the subject support;
assign the body pose as being a prone pose if the subject is face down on the subject support; and
generate a subject pose label comprising at least the body orientation and the body pose.

2. The medical instrument of claim 1, wherein the set of joint location coordinates comprises a left knee joint, and a right knee joint, and a neck joint; wherein the left knee joint coordinate comprises a left knee joint angle with a first restricted range of motion; wherein the right knee joint comprises a right knee joint angle with a second restricted range of motion; wherein the neck joint comprises a neck joint angle with a third restricted range of motion; wherein the decubitus pose is classified as being a left decubitus pose or a right decubitus pose in response to inputting the first restricted range of motion, the second restricted range of motion, and the third restricted range of motion into the predetermined logic module.

3. The medical instrument of claim 1, wherein execution of the machine executable instructions further causes the processor to calculate a decubitus pose deviation from a difference between the predetermined threshold and the torso aspect ratio, and wherein the subject pose label further comprises decubitus pose deviation.

4. The medical instrument of claim 1, wherein the memory further contains a joint locator module configured to construct the set of joint location coordinates in response to receiving an image of the subject on the subject support, wherein execution of the machine executable instructions further causes the processor to:
receive the image of the subject on the subject support;
receive the set of joint location coordinates in response to inputting the image into the joint locator module.

5. The medical instrument of claim 4, wherein the joint locator module contains a neural network configured to output a separate joint location probability map for each of the set of joint location coordinates in response to receiving the image of the subject on the subject support, wherein execution of the machine executable instructions further causes the processor to:
receive the separate joint location probability map in response to inputting the image into the neural network; and
calculate the set of joint location coordinates from the separate joint location probability map for each of the set of joint locations.

6. The medical instrument of claim 5, wherein the medical instrument comprises a camera, wherein execution of the machine executable instructions further causes the camera to acquire the image of the subject on the subject support.

7. The medical instrument of claim 5, wherein execution of machine executable instructions further causes the processor to train the neural network with a set of labeled images, wherein the set of labeled images comprises images of: subjects reposed on a subject support, front views of subjects, rear views of subjects, empty subject supports, subject supports containing medical equipment, and partially obscured images of subjects.

8. The medical instrument of claim 1, wherein the medical instrument further comprises a medical imaging system configured for acquiring medical imaging data from an imaging zone, wherein the subject support is configured for at least partially supporting the subject within the imaging zone.

9. The medical instrument of claim 8, wherein the medical imaging system is any one of the following: a magnetic resonance imaging system, a positron emission tomography system, a single photon emission tomography system, a digital X-ray system, and a computed tomography system.

10. The medical instrument of claim 8, wherein the memory further comprises a medical imaging protocol, wherein the medical imaging protocol comprises a selected pose label, wherein execution of the machine executable instructions further causes the processor to perform any one of the following if the subject pose label differs from the selected pose label:
provide a warning signal; and
select a different medical imaging protocol that comprises the subject pose label;
provide instructions on repositioning the subject; and
combinations thereof.

11. The medical instrument of claim 8, wherein execution of the machine executable instructions further causes the processor to:
control the medical imaging system to acquire medical imaging data;
create an image file comprising the medical imaging data and the subject pose label; and store the image file in a picture archiving and communication system.

12. The medical instrument of claim 1, wherein the medical instrument further comprises a radiotherapy system configured for irradiating targets within an irradiation zone, wherein the subject support is configured to support the subject at least partially within the irradiation zone, wherein the memory further comprises a radiotherapy protocol, wherein the radiotherapy protocol comprises a radiotherapy pose label, wherein execution of the machine executable instructions further causes the processor to perform any one of the following if the subject pose label differs from the radiotherapy pose label:
 provide a warning signal; and
 halt execution of the radiotherapy protocol;
 provide instructions on repositioning the subject; and
 combinations thereof.

13. The medical instrument of claim 1, wherein set of joint location coordinates further comprise: a left elbow joint coordinate and a right elbow joint coordinate, wherein the left elbow joint comprises a left elbow joint angle, wherein the right elbow joint comprises a right elbow joint angle, wherein the left shoulder joint coordinate comprises a left shoulder joint angle, wherein the right shoulder joint coordinate comprises a right shoulder joint angle, wherein execution of the machine executable instructions further causes the processor to receive an arm position classification in response to inputting the right shoulder joint angle, the left shoulder joint angle, the right shoulder joint angle, and the left should joint into the predetermined logic module, wherein the subject pose label further comprises the arm position classification.

14. A method of medical imaging, wherein the method comprises:
 receiving a set of joint location coordinates for a subject reposing on a subject support; wherein the set of joint location coordinates comprises coordinates for: a left hip joint, a right hip joint, a right shoulder joint, and a left shoulder joint;
 receive a body orientation in response to inputting the set of joint location coordinates into a predetermined logic module, wherein the body orientation is head first or feet first relative to a chosen coordinate system;
 calculating a torso aspect ratio from the location of the left hip joint, the right hip joint, the right shoulder joint, and the left shoulder joint;
 wherein if the torso aspect ratio is greater than a predetermined threshold then assign a body pose of the subject as being a decubitus pose;
 wherein if the torso aspect ratio is less than or equal to the predetermined threshold receive a determination if the subject is face up or face down on the subject support in response to inputting the set of joint location coordinates into the predetermined logic model
 assign the body pose as being a supine pose if the subject is face up on the subject support, wherein face up and face down are an orientation of a torso of the subject, wherein face up and face down are an orientation of a torso of the subject, wherein if the subject is face up a back of the subject rests on the subject support, wherein if the subject is face down a chest of the subject rests on the subject support;
 assign the body pose as being a prone pose if the subject is face down on the subject support;
 generating a subject pose label comprising at least the body orientation and the body pose.

15. A non-transitory computer program product comprising machine executable instructions configured to be executed by a processor configured to control a medical instrument, wherein execution of the machine executable instructions causes the processor to:
 receive a set of joint location coordinates for a subject reposing on a subject support; wherein the set of joint location coordinates comprises coordinates for: a left hip joint, a right hip joint, a right shoulder joint, and a left shoulder joint;
 receive a body orientation in response to inputting the set of joint location coordinates into a predetermined logic module-, wherein the body orientation is head first or feet first relative to a chosen coordinate system;
 calculate a torso aspect ratio from the location of the left hip joint, the right hip joint, the right shoulder joint, and the left shoulder joint;
 wherein if the torso aspect ratio is greater than a predetermined threshold then assign a body pose of the subject as being a decubitus pose;
 wherein if the torso aspect ratio is less than or equal to the predetermined threshold receive a determination if the subject is face up or face down on the subject support in response to inputting the set of joint location coordinates into the predetermined logic model-, wherein face up and face down are an orientation of a torso of the subject, wherein face up and face down are an orientation of a torso of the subject, wherein if the subject is face up a back of the subject rests on the subject support, wherein if the subject is face down a chest of the subject rests on the subject support;
 assign the body pose as being a supine pose if the subject is face up on the subject support;
 assign the body pose as being a prone pose if the subject is face down on the subject support; and
 generate a subject pose label comprising at least the body orientation and the body pose.

* * * * *